United States Patent [19]
Craig

[11] 4,038,554
[45] July 26, 1977

[54] DETECTION OF FLAWS IN A MOVING WEB OF TRANSPARENT MATERIAL

[75] Inventor: Dwin R. Craig, Gaithersburg, Md.

[73] Assignee: Columbia Research Corporation, Gaithersburg, Md.

[21] Appl. No.: 665,354

[22] Filed: Mar. 9, 1976

[51] Int. Cl.$^2$ ............................................. G01N 21/32
[52] U.S. Cl. ...................................... 250/572; 356/200
[58] Field of Search ................ 250/216, 562, 563, 572, 250/571; 356/200, 201, 202, 203, 239

[56] References Cited
U.S. PATENT DOCUMENTS

| | | | |
|---|---|---|---|
| 3,743,431 | 7/1973 | Cushing et al. | 356/239 |
| 3,814,946 | 6/1974 | Takahashi et al. | 250/572 |
| 3,849,004 | 11/1974 | Cofek | 250/572 |
| 3,970,857 | 7/1976 | Buckson | 356/200 |

*Primary Examiner*—David C. Nelms

*Attorney, Agent, or Firm*—David H. Semmes; Warren E. Olsen

[57] ABSTRACT

A scanning beam of light is arranged to illuminate a moving web of transparent material wherein the transmitted, undeviated beam falls upon a light absorber. A light collecting rod is located so that only a small amount of the undeviated beam is intercepted. When a transparent refracting flaw arrives in the beam, a portion of the light is deviated and illuminates the light collecting rod which contains a photocell at one end and thereby produces a positive electrical impulse designating the presence of a refracting flaw. When a light absorbing flaw arrives in the beam, illumination of the light collecting rod is reduced which produces a negative electrical impulse designating the presence of an opaque flaw. The difference in signal polarity thereby identifies the type of flaw detected.

14 Claims, 10 Drawing Figures

DETECTION OF FLAWS IN A MOVING WEB OF TRANSPARENT MATERIAL

BACKGROUND OF THE INVENTION

Many systems exist for the detection of flaws in a moving web of material wherein the web is illuminated by a scanning light beam which moves rapidly across the width of the web, combined with a light collecting device and a photocell to sense modulation by the web of light either transmitted or reflected to the photocell. In most cases the photocell output is fed to an elaborate computer designed to identify the size and nature of the flaw detected based on signal characteristics. Most systems fail to recognize the nature of the flaw because the light collecting system does not provide readily distinguishable differences in signal on which the electronic circuitry must operate.

For example, U.S. Pat. No. 3,700,909 in the name of Murray, et al., and of common assignment with the instant invention, employs a photomultiplier tube which receives all of the light which passes through variously sized pinhole defects in a web of opaque material. As taught in this prior patent, the entire amount of light passing through the pinhole is allowed to impinge upon the photomultiplier, thereby determining the amplitude of the photomultipliers signal. Similarly, our prior U.S. Pat. No. 3,755,674, also in the name of Murray, et al., processes a signal generated in response to the amount of light passing through a pinhole defect in an opaque material.

U.S. Pat. No. 3,588,513, in the name of Akamatsu, et al., additionally illustrates a photoelectric inspection system wherein the light reflected, or intercepted, by surface defects on a moving web may be used to generate a variable voltage signal.

U.S. Pat. No. 3,448,279, in the name of Lindemann, et al., represents another type of photoelectric inspection system wherein inspection of a web, such as cloth, is effected by simple light collections, through various transmittance and reflectance sensors, with any subsequent flaw classification requiring involved electronic signal processing equipment.

SUMMARY OF THE INVENTION

This invention is specifically directed to the detection and classification of flaws encountered in the manufacture of transparent material in the form of thin plastic film. Such films contain two basic types of flaws, namely 1) foreign materials 2) undissolved solids. Foreign materials, such as specks of imbedded dust or dirt, tend to be opaque to light. Undissolved or partially dissolved solids are generally composed of the same material from which the film is formed, but for some reason have not become homogenous with the surrounding material and therefore have not reached the desired degree of transparency. Instead, and in distinction to opaque flaws, such undissolved transparent material aggregations tend to change the direction of an incident beam-deviation by refraction.

Prior systems, such as those exemplified, above, which collect light from the main beam, cannot distinguish between these two types of flaws, since each type of flaw tends to reduce the intensity of light received by the photocell.

It is the purpose of this invention to provide a system which will produce a different polarity of signal for each of the two different types of flaws. In short, a foreign body will reduce the amount of light reaching the photocell whereas an undissolved solid will increase the light reaching the photocell. The difference in polarity of the resulting electrical signal will allow the following circuitry to easily distinguish between the two basic types of flaws. Furthermore, the amount of reduction and the amount of increase will indicate the size of the flaw.

The ability to accomplish the above-desired result is significantly derived from a novel method of illuminating the film and of collecting the light after transmission by the film.

Further objects and advantages of the invention may be more fully understood by the following description of a preferred embodiment, illustrated by way of example in the accompanying drawings.

DESCRIPTION OF THE PREFERRED EMBODIMENTS

Figure 1:
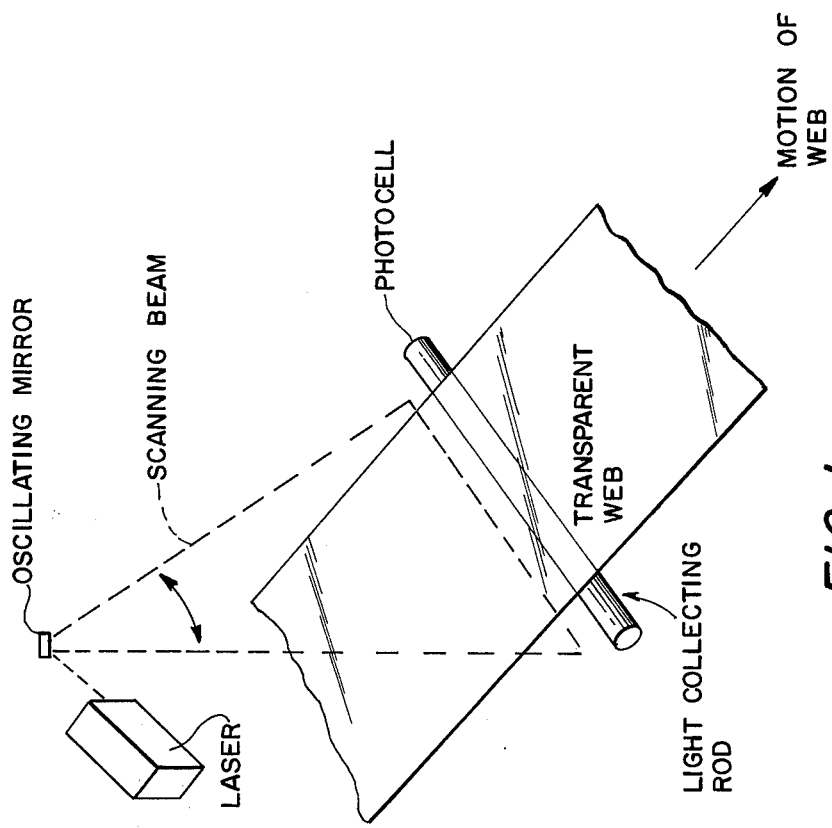
FIG. 1 is a schematic illustration of the basic elements of a system for detecting and classifying flaws within a moving web of transparent material as contemplated herein.

According to the method and apparatus for the practice of the invention, a moving web of transparent material is illuminated by a scanning beam of light, incident at right angles to a top surface of the film, and moved rapidly back and forth across the width of the film, as broadly configured in FIG. 1. The present invention requires the light distribution within the scanning beam to consist of a relatively narrow, high intensity central core, symmetrical about an axis colinear with the beam direction, and surrounded by a large, low intensity disk, such as that produced by a LASER, or by an extremely coherent beam of light projected from a cathode ray tube.

Figure 2:
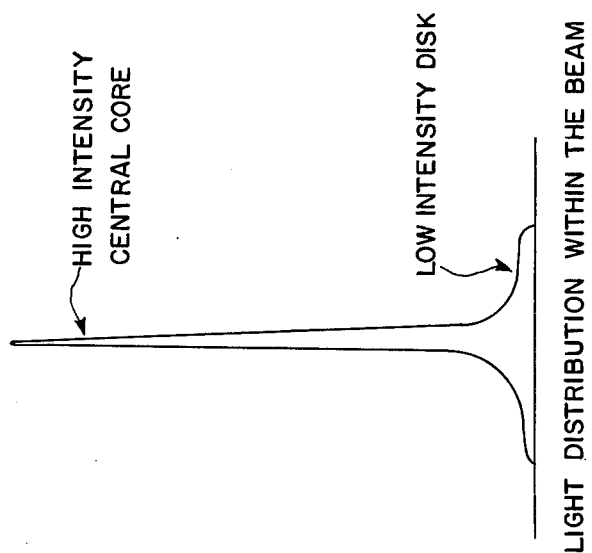
FIG. 2 schematically illustrates the light distribution of a scanning beam required according to the present invention.

FIG. 2 represents the desired relative magnitudes of light fall-off for a substantially coherent light source usable according to the present invention. As illustrated, the beam is virtually symmetrical about its high intensity centerline, so that that area of impingement for the high intensity central core is significantly less than the surrounding annular area of impingement for the low intensity portion of the beam.

Figure 3:
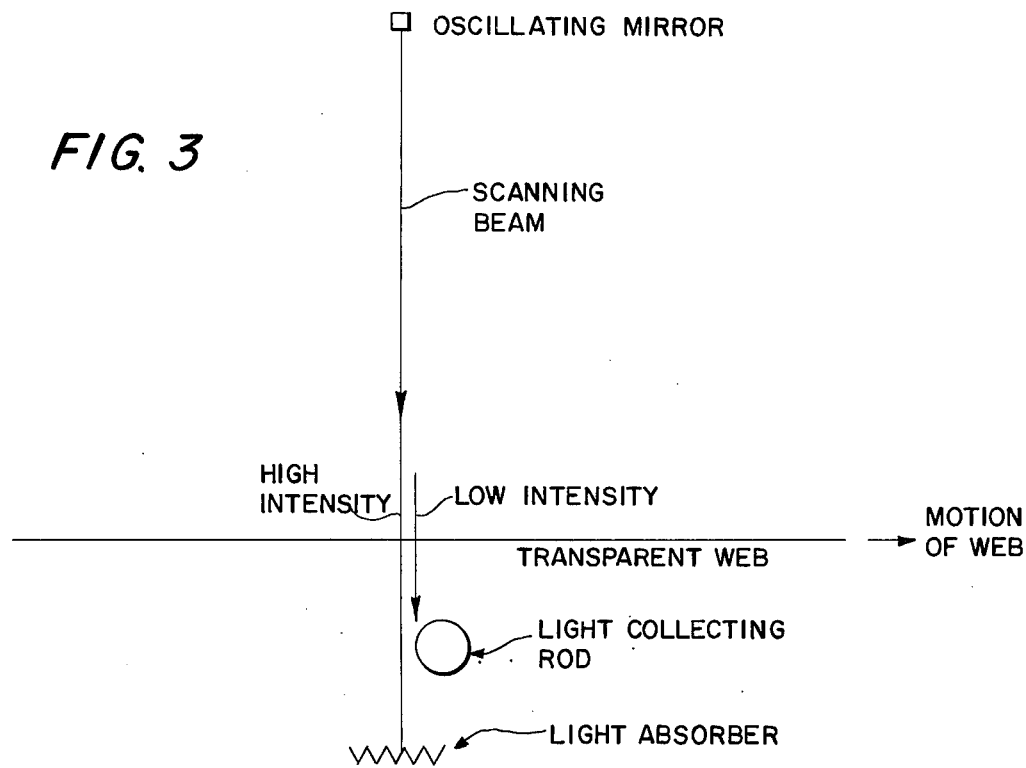
FIG. 3 schematically represents one embodiment according to the present invention.

With reference to FIG. 3, the respective juxapositioning of the essential components, according to a first embodiment of the invention, are illustrated and identified. A web of transparent material is illustrated as moving horizontally, and, for purposes of illustration, may be any form of non-opaque plastic film. As used herein, transparent is, of course, intended to be with reference to the ability of the web material to optically transmit the frequency of the light produced by the associated light beam. According to the preferred embodiments herein, an 'undissolved solid' is used to denote a localized agglomeration of that transparent material of which the web is comprised. For example, if the web comprises a thin film, of acrylic plastic, localized transparent imperfections may be due to the inclusion of entrained air bubbles or undissolved, yet transparent, resin particles. Additionally, a transparent flaw may result from a localized variation in web thickness due to 'undissolved solid' mass of transparent material, causing a net light deviation through the non-planar upper and lower web surfaces associated with the localized thickness variation.

FIG. 3 further illustrates that the high intensity portion of the scanning beam will not impinge upon the light collecting rod, if the scanned beam remains colinear after having been normally directed against the plane of the moving transparent web. If undeviated by a refractive flaw, within the transparent web, the high intensity portion of the scanning beam will remain in a plane which is both normal to the plane of the web and parallel to the centerline of the light collecting rod.

One light collecting rod is shown with its centerline positioned below, and parallel to, the horizontal plane of travel for the transparent film, at a known distance therefrom. Since the light collecting rod is also parallel to the plane of the scanning beam, two critical relationships are established. Firstly, the relatively narrow high intensity core of a beam, with the distribution of FIG. 2, will normally miss the rod, and fall onto a passive light absorber device, and, secondly, at least part of the annular, and relatively large low intensity disk will normally fall on the rod and be directed to the photocell. This normal impingement of only the low intensity disk provides a constant, but low, light level to the photocell which, in turn, produces a D.C. voltage signal which will be intermediate between that caused by a fully deviated and a fully absorbed beam, as explained more fully hereinafter. It is evident that a light absorbing flaw will produce a "dark going", or relatively negative voltage signal and that a light refracting flaw will produce a "bright going", or relatively positive voltage signal, this categorical distinction in the type of flaw within a transparent web will result in electrical pulses having opposite polarity, relative to the intermediate D.C. voltage. This result has been proven experimentally, and it has further been discovered that the relationship of flaw size to beam size is different, and classifiable, as between the two types of flaws.

It is well recognized that the amplitude of the photoelectric signal produced by any light absorbing flaw area, will be directly proportional to the area fraction of the impingement area of the beam which the flaw occupies. Significantly, therefore, if a beam is used, as in the prior art systems, with the high intensity core of the beam normally being used to sense the presence of all light absorbing flaws, the reduction in signal amplitude so generated will be directly proportional to the relative area of the high intensity core which is occupied by the light absorbing flaw. As has been noted, both light absorbing flaws and light refracting flaws will reduce the intensity of a given, constant intensity light source impinging thereon.

Figure 4:
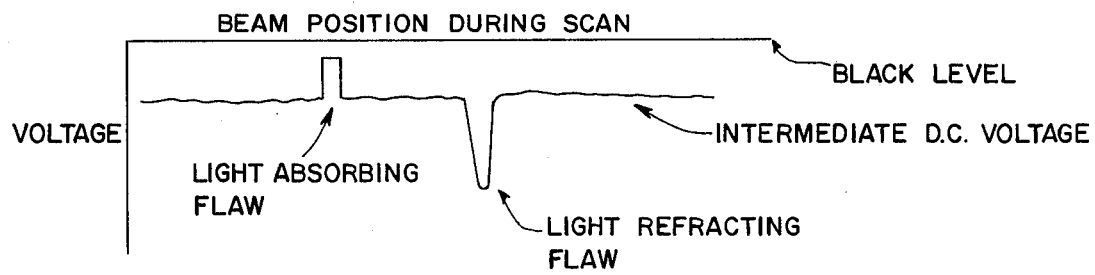
FIG. 4 graphically represents the invention in voltage polarity, about an intermediate voltage, produced according to the present invention.
Figure 5:
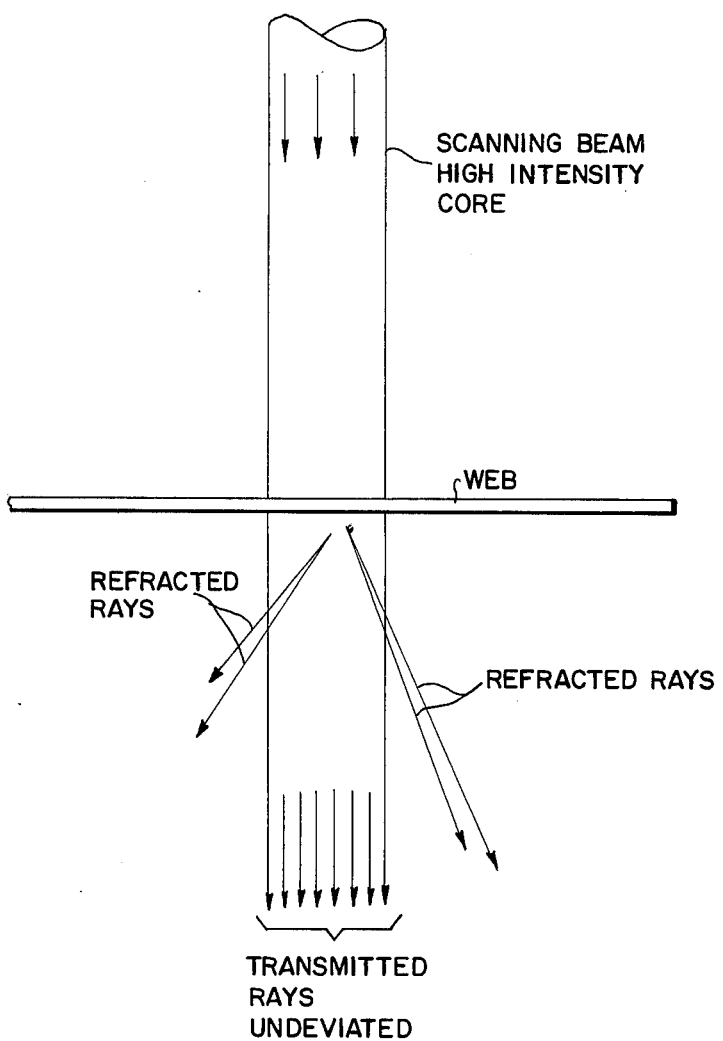
FIG. 5 is a schematic representation of a particularly advantageous feature contemplated by the present invention.
Figure 6:
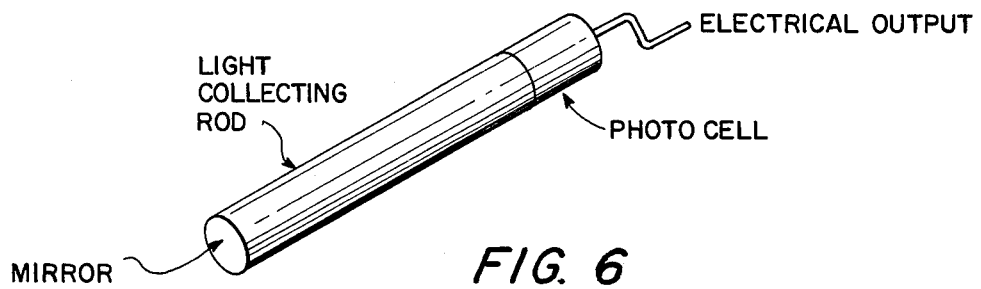
FIG. 6 schematically represents one form of light collecting rod usable with the present invention.
Figure 7:
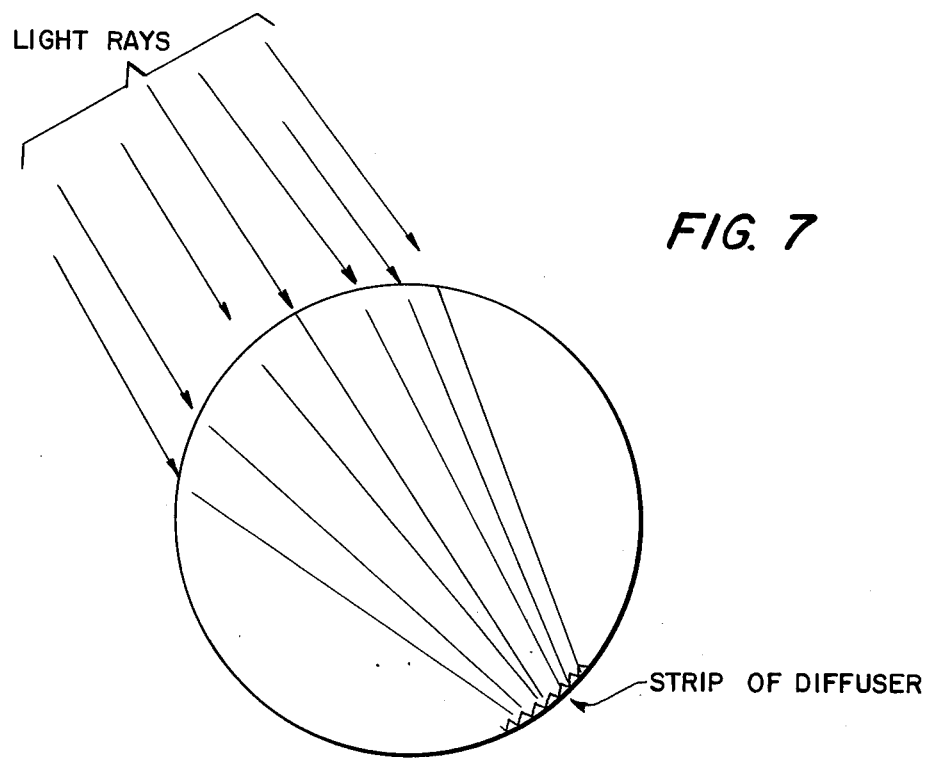
FIG. 7 schematically represents a transverse section view of the rod illustrated in FIG. 6.
Figure 8:
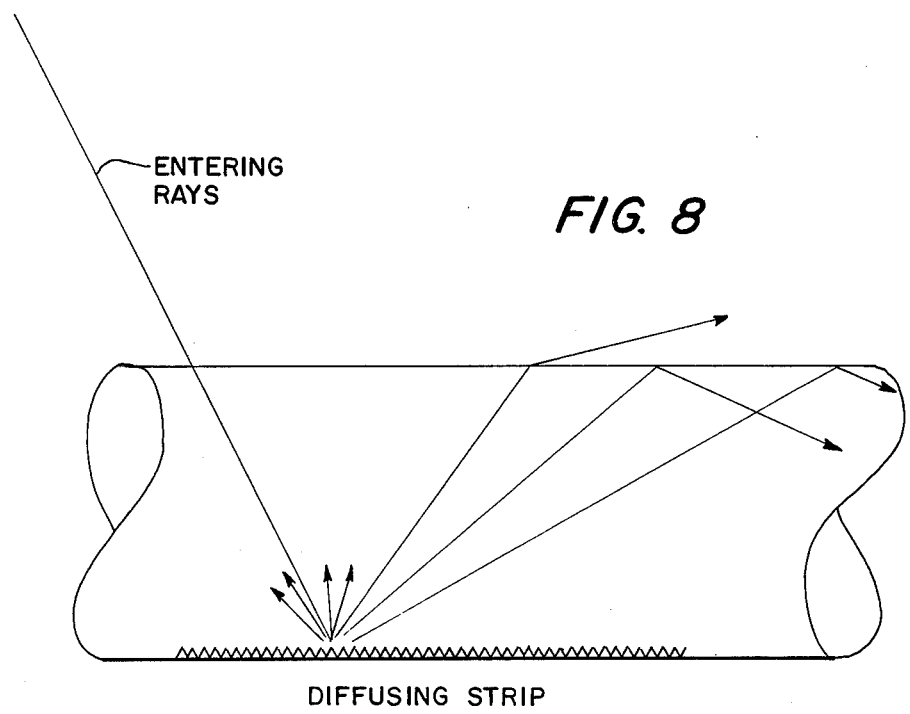
FIG. 8 schematically represents a longitudinal section view of the rod illustrated in FIG. 6.

According to the invention taught herein, light absorbing flaws in the web will mask at least a portion of the low intensity disk, thereby producing the relatively negative voltage illustrated in FIG. 4. However, as a further significant advantage of the present invention, even light refracting flaws which are much smaller than the beam can be detected. This synergistic result is represented by the schematic illustration in FIG. 5. Although only a small fraction of the total cross-sectional area of the main beam may be deviated toward the light collecting rod, its intensity may be several hundred times as great as that from the low intensity disk which normally illuminates the rod. As shown in FIG. 2, the steep intensity change, between the central core and disc, would significantly affect the surface of a photocell. A simple form of light collecting rod, operable for use in the present invention, is illustrated in FIGS. 6-8 and consists of a cylinder of solid transparent material with a mirror bonded at one end and a photocell at the other. The transparent rod may then serve both as a collector and a conduit for any light impinging thereon. The collection feature resides in the fact that any light directed toward the rod will tend to be focused at, or near, its rear surface. This optical result is illustrated in FIG. 7 as due to refraction of the incident light by the cylindrical rod walls, and the relatively high index of refraction of these walls with respect to the surrounding atmosphere. However, with simply a transparent rod, the light would then pass through the rear surface with none being directed toward a photocell, or mirror, at either end. In order to cause the incident light to be directed, in part, along the length of the rod, a narrow strip of diffusing material is bonded to the rod for its full length, to function as a light diffuser, as shown in FIG. 8. Some of the diffused light will be redirected toward the surface of the rod at angles which will produce total internal reflection and, thus, proceed ultimately to the photocell. This well-known phenomenon may also be described as the "greenhouse" effect.

For optimum performance as a collector, the rod should be made of a transparent material with a high index of refraction, so that incident light will tend to focus near the rearmost inner surface of the rod walls. For optimizing performance of the rod, as a light conduit, the surface of the rod should be polished, the width of the diffusing strip should be kept small, as compared to the circumference to the rod, and the material of the rod should have high transmissivity for the dominant wavelengths of light beam being used.

Figure 9:
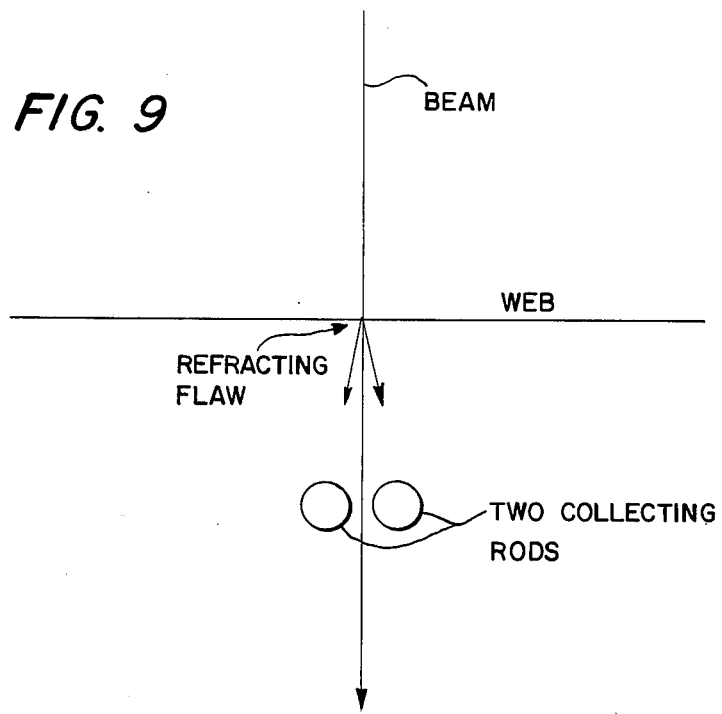
FIG. 9 schematically represents a second embodiment according to the present invention.

Previous description has referred to a single rod, but it is clear that more than one rod could be used to improve the light collection efficiency, hence sensitivity for refracting flaws. For example, FIG. 9 illustrates a second embodiment with two rods in parallel, and positioned so that the high intensity portion of the beam normally falls between them, and is absorbed. With such an arrangement, the opportunity for sensing light refracted by a flaw of the light refracting category would be doubled.

Figure 10:
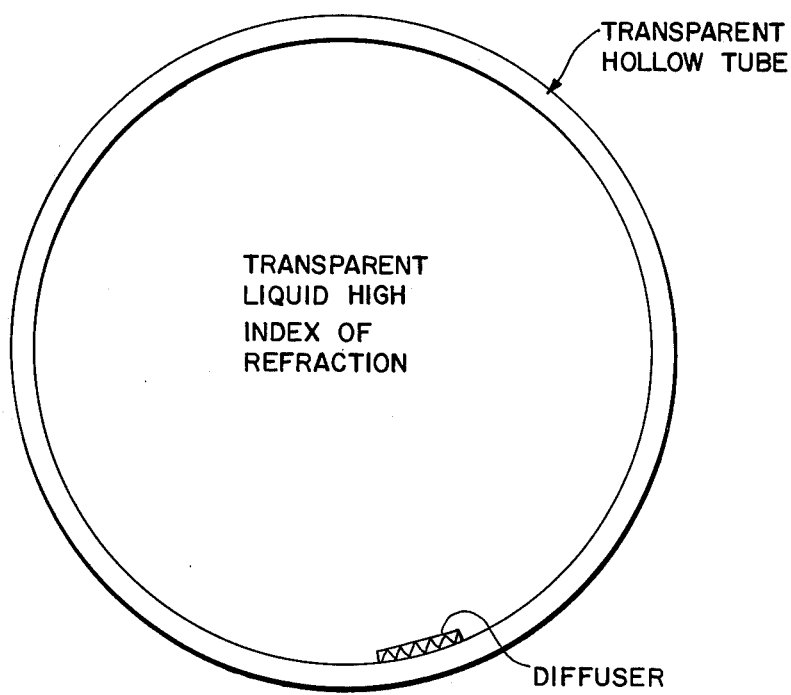
FIG. 10 schematically represents a second form of light collector usable with the present invention.

An alternate construction for a light collecting rod is illustrated in FIG. 10 as comprising a transparent tube filled with a transparent liquid. If the index of refraction of the liquid is chosen to be equal to, or greater than, that of the tube, the conduit efficiency will be improved, according to well-known principles of fiber optics.

While a preferred embodiment of the invention has been illustrated in the drawings and particularly described, it will be understood that the invention is in no way limited to this embodiment and that modifications may be made within the scope of the appended claims.

I claim:

1. A method for detection of flaws in a substantially planar web of transparent material, said method being characterized by being able to distinguish between the presence of a light absorbing flaw, and a light refracting flaw, in said material, comprising the steps of:
   A. directing a light beam upon one surface of said web of transparent material with a beam direction that is within a plane that is perpendicular to the plane of said web; wherein,
   B. said light beam has a light distribution further comprising a high intensity central cores, symmetrical about an axis colinear with said beam direction, and surrounded by an annular disk of significantly lower intensity; and
   C. passively absorbing all of said high intensity light distribution which remains directed in the plane of said beam direction after passing through said transparent web material; while
   D. impinging at least a portion of that low intensity disk, which remains directed in the plane of said beam direction after passing through said web, onto a photoelectric signal generating means; and
   E. generating a constant intermediate signal in said photoelectric signal generating means in response to the said impingement of said low intensity disk, whereby a light refracting flaw is operable to deviate said high intensity core to produce a signal of a first polarity, and a light absorbing flaw is operable to generate a signal of the opposite polarity.

2. The method according to claim 1 wherein the high intensity central core of said directed light beam is more than one hundred times greater in intensity than said surrounding annular disk.

3. The method according to claim 1 wherein said step of directing said light beam further comprises scanning said beam in a plane perpendicular to a plane of movement for said transparent web, and said photoelectric signal generating means further comprises a light collecting rod parallel to the plane of said scanned beam.

4. The method according to claim 3 wherein said step of directing a scanned beam further comprises generating said beam with a stationary light source and oscillating said beam, from a point which is spaced substantially above said one surface, so said beam is perpendicular to the direction of movement of said moving web of transparent material.

5. The method according to claim 3 wherein said step of impinging that portion of the low intensity disk, which remains directed in the plane of said beam direction after passing through said transparent web, further comprises diffusing a portion of said impinged light within said light collecting rod and internally reflecting a least a portion of said impinged light to at least one end of said collecting rod.

6. The method according to claim 5 wherein said internally reflected light is passed through a liquid of relatively high refractive index contained within said light collecting rod.

7. An apparatus for detection of flaws within a substantially planar web of transparent material, characterized by structure operable for the generation of signals wherein the polarity of the signal distinguishes between the presence of a light absorbing flaw and a light refracting flaw in said web, and comprising, in combination:
   A. means to direct a light beam upon one surface of said web of transparent material with a beam direction that is within a plane that is perpendicular to the plane of said web; wherein
   B. said light beam comprises a high light intensity central core, symmetrical about an axis colinear with said beam direction, and surrounded by an annular disk of significantly lower light intensity; and
   C. a passive light absorbing means, located below the opposite surface of said web, and positioned with respect to the direction of said light beam so as to absorb all of said high intensity central core which remains directed in the plane of said beam direction after passing through said transparent web meterial; and
   D. a photoelectric signal generating means located below the opposite surface of said moving web and positioned, with respect to at least a portion of said directed annular disk of significantly lower light intensity, to allow an impingement of that portion of said annular disk which remains directed in the plane of said beam direction after passing through said transparent web; wherein
   E. said photoelectric signal generating means includes means to generate an intermediate signal in response to said disk impingement, whereby a light refracting flaw is operable to deviate said high intensity core onto said photoelectric signal generating means to produce a signal of a first polarity, and a light absorbing flaw is operable to generate a signal of the opposite polarity.

8. An apparatus according to claim 7 wherein the central core of said directed light beam has an intensity more than one hundred times the intensity of said surrounding annular disk.

9. An apparatus according to claim 7 wherein the means to direct said light beam further includes means to scan beam in a plane perpendicular to a plane of movement of said transparent web, and said photoelectric signal generating means further comprises at least one light collecting rod parallel to and spaced from the plane of said scanned beam.

10. An apparatus according to claim 9 wherein said means to direct said beam further comprises a stationary light source and an oscillating mirror, spaced substantially above said one web surface, and operable to scan said beam in a direction perpendicular to the direction of movement of said moving web.

11. An apparatus according to claim 9 wherein said light collecting rod includes a diffuser, on an inner wall, operable to diffuse a portion of the light impinging thereon and allow at least a portion of said impinged light to internally reflect towards either end of said rod.

12. An apparatus according to claim 11 wherein one end of said light collecting rod further comprises a light reflecting surface, and the opposite end further comprises a photocell.

13. An apparatus according to claim 10 wherein said stationary light source comprises a laser.

14. An apparatus according to claim 12 wherein said light collecting rod further includes a hollow cylindrical member, a transparent material, with a liquid of relatively high refractive index therein.

* * * * *